United States Patent
Wahlstrand et al.

(10) Patent No.: US 7,529,586 B2
(45) Date of Patent: *May 5, 2009

(54) CONCAVITY OF AN IMPLANTABLE MEDICAL DEVICE

(75) Inventors: Carl D. Wahlstrand, Lino Lakes, MN (US); Darren A. Janzig, Centerville, MN (US); Ruchika Singhal, Minneapolis, MN (US); Robert M. Skime, Coon Rapids, MN (US); Erik R. Scott, Maple Grove, MN (US); James E. Randall, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/731,867

(22) Filed: Dec. 9, 2003

(65) Prior Publication Data

US 2004/0176673 A1   Sep. 9, 2004

Related U.S. Application Data

(60) Provisional application No. 60/507,857, filed on Oct. 1, 2003, provisional application No. 60/503,946, filed on Sep. 20, 2003, provisional application No. 60/503,945, filed on Sep. 20, 2003, provisional application No. 60/471,262, filed on May 16, 2003, provisional application No. 60/431,854, filed on Dec. 9, 2002.

(51) Int. Cl.
*A61N 1/36* (2006.01)

(52) U.S. Cl. .................................................. 607/36

(58) Field of Classification Search ............. 607/45, 607/57, 2, 36–38, 116, 46; 623/11.11, 10; D24/155, 187, 189; 600/25
See application file for complete search history.

(56) References Cited

U.S. PATENT DOCUMENTS 3,690,325 A   9/1972   Kenny ................. 607/36

(Continued)

FOREIGN PATENT DOCUMENTS

DE   3940632   12/1990

(Continued)

OTHER PUBLICATIONS

Notification of Transmittal of the International Search Report dated May 7, 2004, International Application No. PCT/US03/38982.

(Continued)

*Primary Examiner*—Carl H Layno
*Assistant Examiner*—Jessica Reidel
(74) *Attorney, Agent, or Firm*—John W. Albrecht; Medtronic, Inc.

(57) ABSTRACT

At least one surface of an implantable medical device is concave along at least one axis such that it substantially conforms to a surface within a patient, such as the cranium, when it is implanted on that surface. In some embodiments, the surface of the implantable medical device substantially conforms to an arc with a radius that is between 4.5 and 9.5 centimeters, and is preferably approximately equal to 7 centimeters. In some embodiments, the implantable medical device comprises a plurality of interconnected modules, and an overmold that at least partially encapsulates each of the modules. In such embodiments, at least one surface of the overmold is concave along at least one axis. Further, each of the modules of such an implantable medical device may comprise a housing, and at least one surface of at least one of the housings may be concave along at least one axis.

24 Claims, 10 Drawing Sheets

U.S. PATENT DOCUMENTS

| | | | |
|---|---|---|---|
| 3,720,874 A | 3/1973 | Gorcik et al. | |
| 3,724,467 A | 4/1973 | Avery et al. | 607/117 |
| 3,888,260 A * | 6/1975 | Fischell | 607/36 |
| 3,913,587 A | 10/1975 | Newash | 604/8 |
| 3,926,198 A * | 12/1975 | Kolenik | 607/36 |
| 4,010,760 A | 3/1977 | Kraska et al. | |
| 4,013,081 A | 3/1977 | Kolenik | 607/9 |
| 4,040,412 A | 8/1977 | Sato | 600/391 |
| 4,094,321 A * | 6/1978 | Muto | 607/36 |
| 4,256,115 A | 3/1981 | Bilitch | |
| 4,266,552 A | 5/1981 | Dutcher et al. | 607/113 |
| 4,328,813 A | 5/1982 | Ray | 607/139 |
| 4,399,819 A | 8/1983 | Cowdery | 607/9 |
| 4,399,820 A | 8/1983 | Wirtzfeld et al. | |
| 4,499,907 A | 2/1985 | Kallok et al. | |
| 4,616,655 A | 10/1986 | Weinberg et al. | 607/2 |
| 4,911,178 A | 3/1990 | Neal | 607/115 |
| 4,928,696 A | 5/1990 | Henderson et al. | |
| 4,934,368 A | 6/1990 | Lynch | |
| 4,969,899 A | 11/1990 | Cox | 623/8 |
| 4,972,846 A | 11/1990 | Owens et al. | |
| 5,085,644 A | 2/1992 | Watson et al. | 144/162 |
| 5,144,946 A | 9/1992 | Weinberg et al. | |
| 5,197,332 A | 3/1993 | Shennib | |
| 5,220,929 A | 6/1993 | Marquit | |
| 5,243,977 A * | 9/1993 | Trabucco et al. | 607/10 |
| 5,252,090 A | 10/1993 | Giurtino et al. | |
| 5,271,397 A | 12/1993 | Seligman et al. | 607/137 |
| 5,312,440 A | 5/1994 | Hirschberg et al. | |
| 5,314,451 A | 5/1994 | Mulier | 607/133 |
| 5,314,453 A | 5/1994 | Jeutter | |
| 5,411,537 A | 5/1995 | Munshi et al. | |
| H1465 H | 7/1995 | Stokes | |
| 5,433,734 A | 7/1995 | Stokes et al. | |
| 5,455,999 A | 10/1995 | Weiss et al. | 29/623.1 |
| 5,456,698 A * | 10/1995 | Byland et al. | 607/36 |
| 5,480,416 A | 1/1996 | Garcia et al. | |
| 5,489,225 A | 2/1996 | Julian | 439/837 |
| 5,554,194 A | 9/1996 | Sanders | 603/17.17 |
| 5,562,715 A | 10/1996 | Czura et al. | 607/36 |
| 5,571,148 A | 11/1996 | Loeb et al. | 607/57 |
| 5,613,935 A | 3/1997 | Jarvik | |
| 5,638,832 A | 6/1997 | Singer et al. | |
| 5,645,586 A | 7/1997 | Meltzer | 623/11.11 |
| 5,674,260 A | 10/1997 | Weinberg | |
| 5,678,559 A | 10/1997 | Drakulic | |
| 5,702,430 A | 12/1997 | Larson, Jr. et al. | 607/61 |
| 5,741,313 A | 4/1998 | Davis et al. | 607/36 |
| 5,755,743 A | 5/1998 | Volz et al. | |
| 5,769,874 A | 6/1998 | Dahlberg | |
| 5,776,169 A | 7/1998 | Schroeppel | |
| 5,792,067 A | 8/1998 | Karell | 600/534 |
| 5,800,535 A | 9/1998 | Howard, III | 623/10 |
| 5,814,095 A | 9/1998 | Müller et al. | 607/57 |
| 5,843,150 A | 12/1998 | Dreessen et al. | 607/116 |
| 5,873,899 A | 2/1999 | Stutz, Jr. et al. | |
| RE36,120 E | 3/1999 | Karell | 607/36 |
| 5,876,424 A * | 3/1999 | O'Phelan et al. | 607/36 |
| 5,895,414 A | 4/1999 | Sanchez-Zambrano | 607/36 |
| 5,896,647 A | 4/1999 | Shkuratoff | 29/623.2 |
| 5,919,215 A | 7/1999 | Wiklund et al. | 607/36 |
| 5,935,154 A | 8/1999 | Westlund | 607/57 |
| 5,941,905 A | 8/1999 | Single | 607/66 |
| 5,941,906 A | 8/1999 | Barreras, Sr. et al. | 607/66 |
| 5,954,751 A | 9/1999 | Chen et al. | |
| 5,954,757 A | 9/1999 | Gray | |
| 5,984,859 A | 11/1999 | Lesinski | 600/25 |
| 5,991,664 A | 11/1999 | Seligman | 607/90 |
| 6,006,124 A | 12/1999 | Fischell et al. | 600/378 |
| 6,016,449 A | 1/2000 | Fischell et al. | 607/45 |
| 6,016,593 A | 1/2000 | Kyrstein | 29/401.1 |
| 6,044,304 A | 3/2000 | Baudino | |
| 6,061,593 A | 5/2000 | Fischell et al. | 600/544 |
| 6,067,474 A | 5/2000 | Schulman et al. | 607/57 |
| 6,091,979 A | 7/2000 | Madsen | 600/377 |
| 6,128,538 A | 10/2000 | Fischell et al. | 607/45 |
| 6,131,581 A * | 10/2000 | Leysieffer et al. | 128/899 |
| 6,134,474 A | 10/2000 | Fischell et al. | 607/45 |
| 6,162,487 A | 12/2000 | Darouiche | |
| 6,168,580 B1 | 1/2001 | Yardley | 604/265 |
| 6,176,879 B1 | 1/2001 | Reischl et al. | 623/11.11 |
| 6,214,032 B1 | 4/2001 | Loeb et al. | 607/1 |
| 6,218,016 B1 | 4/2001 | Tedeschi et al. | |
| 6,230,049 B1 | 5/2001 | Fischell et al. | 600/544 |
| 6,248,080 B1 | 6/2001 | Miesel et al. | 600/561 |
| 6,259,951 B1 | 7/2001 | Kuzma et al. | 607/57 |
| 6,263,225 B1 | 7/2001 | Howard, III | |
| 6,266,556 B1 * | 7/2001 | Ives et al. | 600/544 |
| 6,269,266 B1 | 7/2001 | Leysieffer | 607/2 |
| 6,272,382 B1 | 8/2001 | Faltys et al. | 607/57 |
| 6,308,101 B1 | 10/2001 | Faltys et al. | 607/57 |
| 6,324,428 B1 | 11/2001 | Weinberg et al. | 607/36 |
| 6,330,468 B1 | 12/2001 | Scharf | |
| 6,354,299 B1 | 3/2002 | Fischell et al. | 128/899 |
| 6,356,792 B1 | 3/2002 | Errico et al. | |
| 6,358,281 B1 | 3/2002 | Berrang et al. | 623/10 |
| 6,360,122 B1 | 3/2002 | Fischell et al. | 600/544 |
| 6,405,079 B1 | 6/2002 | Ansarinia | |
| 6,427,086 B1 | 7/2002 | Fischell et al. | 607/45 |
| 6,436,422 B1 | 8/2002 | Trogolo et al. | |
| 6,445,956 B1 | 9/2002 | Laird et al. | |
| 6,456,886 B1 | 9/2002 | Howard et al. | |
| 6,480,743 B1 | 11/2002 | Kirkpatrick et al. | 607/45 |
| 6,490,486 B1 | 12/2002 | Bradley | |
| 6,516,227 B1 | 2/2003 | Meadows et al. | 607/46 |
| 6,517,476 B1 | 2/2003 | Bedoya et al. | |
| 6,537,200 B2 | 3/2003 | Leysieffer et al. | 600/25 |
| 6,554,762 B2 | 4/2003 | Leysieffer | 600/25 |
| 6,560,486 B1 | 5/2003 | Osorio et al. | 607/45 |
| 6,565,503 B2 | 5/2003 | Leysieffer et al. | 600/25 |
| 6,567,703 B1 | 5/2003 | Thompson et al. | |
| 6,575,894 B2 | 6/2003 | Leysieffer et al. | 600/25 |
| 6,597,954 B1 | 7/2003 | Pless et al. | |
| 6,618,623 B1 | 9/2003 | Pless et al. | |
| 6,626,680 B2 | 9/2003 | Ciurzynski et al. | 437/874 |
| 6,648,914 B2 | 11/2003 | Berrang et al. | 623/10 |
| 6,671,544 B2 | 12/2003 | Baudino | |
| 6,726,678 B1 | 4/2004 | Nelson et al. | 604/891.1 |
| 6,788,974 B2 * | 9/2004 | Bardy et al. | 607/36 |
| 6,805,998 B2 | 10/2004 | Jenson et al. | |
| 6,882,881 B1 | 4/2005 | Lesser et al. | |
| 6,963,780 B2 | 11/2005 | Ruben et al. | |
| 6,977,124 B2 | 12/2005 | Probst et al. | |
| 6,994,933 B1 | 2/2006 | Bates | |
| 7,010,351 B2 | 3/2006 | Firlik et al. | |
| 7,103,415 B2 | 9/2006 | Probst et al. | |
| 7,107,097 B2 | 9/2006 | Stern et al. | |
| 7,212,864 B2 * | 5/2007 | Wahlstrand et al. | 607/36 |
| 7,242,982 B2 * | 7/2007 | Singhal et al. | 607/36 |
| 7,263,401 B2 | 8/2007 | Scott et al. | |
| 2001/0033953 A1 | 10/2001 | Gan et al. | 429/9 |
| 2001/0051819 A1 | 12/2001 | Fischell et al. | 607/45 |
| 2002/0002390 A1 | 1/2002 | Fischell et al. | 607/45 |
| 2002/0013612 A1 | 1/2002 | Whitehurst | 607/45 |
| 2002/0019669 A1 | 2/2002 | Berrang et al. | 623/10 |
| 2002/0042634 A1 | 4/2002 | Bardy et al. | |
| 2002/0051550 A1 | 5/2002 | Leysieffer | 381/322 |
| 2002/0068958 A1 * | 6/2002 | Bardy et al. | 607/5 |
| 2002/0072770 A1 | 6/2002 | Pless | 607/2 |
| 2002/0077670 A1 | 6/2002 | Archer et al. | 607/45 |
| 2002/0087201 A1 | 7/2002 | Firlik et al. | |
| 2002/0099412 A1 | 7/2002 | Fischell et al. | 607/3 |
| 2002/0103510 A1 | 8/2002 | Bardy et al. | 607/5 |
| 2002/0107546 A1 * | 8/2002 | Ostroff et al. | 607/5 |

| | | | |
|---|---|---|---|
| 2002/0165588 A1 | 11/2002 | Fraley et al. | 607/37 |
| 2003/0004428 A1 | 1/2003 | Pless et al. | 600/544 |
| 2003/0004546 A1 | 1/2003 | Casey | 607/1 |
| 2003/0017372 A1* | 1/2003 | Probst et al. | 429/7 |
| 2003/0040781 A1 | 2/2003 | Larson et al. | 607/36 |
| 2003/0073972 A1 | 4/2003 | Rosenman et al. | |
| 2003/0085684 A1 | 5/2003 | Tsukamoto et al. | 320/108 |
| 2003/0088294 A1 | 5/2003 | Gesotti | 607/45 |
| 2003/0109903 A1 | 6/2003 | Berrang et al. | 607/36 |
| 2003/0120320 A1 | 6/2003 | Solom | |
| 2003/0125786 A1 | 7/2003 | Gliner et al. | |
| 2003/0130706 A1 | 7/2003 | Sheffield et al. | |
| 2003/0171787 A1 | 9/2003 | Money et al. | 607/57 |
| 2003/0204229 A1 | 10/2003 | Stokes | |
| 2004/0082977 A1 | 4/2004 | Engmark et al. | |
| 2004/0102828 A1 | 5/2004 | Lowry et al. | |
| 2004/0176814 A1* | 9/2004 | Singhal et al. | 607/45 |
| 2004/0176815 A1 | 9/2004 | Janzig et al. | |
| 2004/0176818 A1* | 9/2004 | Wahlstrand et al. | 607/45 |
| 2004/0181263 A1 | 9/2004 | Balzer et al. | |
| 2004/0186528 A1 | 9/2004 | Ries et al. | |
| 2005/0033378 A1 | 2/2005 | Sheffield et al. | |
| 2005/0070971 A1 | 3/2005 | Fowler et al. | |
| 2005/0075679 A1 | 4/2005 | Gliner et al. | |
| 2006/0116743 A1 | 6/2006 | Gibson et al. | |
| 2006/0129205 A1 | 6/2006 | Boveja et al. | |

FOREIGN PATENT DOCUMENTS

| | | |
|---|---|---|
| EP | 1 145 735 A2 | 10/2001 |
| EP | 1 145 736 A2 | 10/2001 |
| GB | 1 161 579 | 8/1969 |
| WO | WO 92/20402 | 11/1992 |
| WO | WO 00/13743 | 3/2000 |
| WO | WO 01/10369 | 2/2001 |
| WO | WO 01/28622 | 4/2001 |
| WO | WO 01/39830 | 6/2001 |
| WO | WO 01/41858 | 6/2001 |
| WO | WO 01/97906 | 12/2001 |
| WO | WO 02/05590 | 1/2002 |
| WO | WO 02/056637 | 7/2002 |
| WO | WO 03/026739 | 4/2003 |
| WO | WO 03/076012 | 9/2003 |
| WO | WO 2004/043536 | 5/2004 |
| WO | 2004/052459 A1 | 6/2004 |
| WO | WO 2004/052458 | 6/2004 |

OTHER PUBLICATIONS

Written Opinion dated Dec. 16, 2004, International Application No. PCT/US03/38982.
Notification of Transmittal of the International Preliminary Examination Report dated Apr. 11, 2005, International Application No. PCT/US03/38982.
U.S. Appl. No. 10/837,319, filed Apr. 30, 2004, entitled "Implantable Medical Device With Anti-Infection Agent."
U.S. Appl. No. 10/835,527, filed Apr. 29, 2004, entitled as "Implantation of Implantable Medical Device".
U.S. Appl. No. 10/835,232, filed Apr. 29, 2004, entitled "Explanation of Implantable Medical Device."
U.S. Appl. No. 10/835,233, filed Apr. 29, 2004, entitled "Implantable Medical Device With A Nonhermetic Battery."
U.S. Appl. No. 10/835,548, filed Apr. 29, 2004, entitled "Headset Recharger For Cranially Implantable Medical Devices."
U.S. Appl. No. 10/835,245, filed Apr. 29, 2004, entitled "Battery Housing Configuration."
U.S. Appl. No. 10/837,276, filed Apr. 30, 2004, entitled "Implantable Medical Device With Lubricious Material."
U.S. Appl. No. 10/731,868, filed Dec. 9, 2003, entitled "Implantation of Low-Profile Implantable Medical Device."
U.S. Appl. No. 10/731,699, filed Dec. 9, 2003, entitled "Coupling Module of a Modular Implantable Medical Device."
U.S. Appl. No. 10/730,873, filed Dec. 9, 2003, entitled "Overmold for a Modular Implantable Medical Device."
U.S. Appl. No. 10/731,881, filed Dec. 9, 2003, entitled "Reducing Relative Intermodule Motion in a Modular Implantable Medical Device."
U.S. Appl. No. 10/730,878, filed Dec. 9, 2003, entitled "Lead Interconnect Module of a Modular Implantable Medical Device."
U.S. Appl. No. 10/730,877, filed Dec. 9, 2003, entitled "Low-Profile Implantable Medical Device."
U.S. Appl. No. 10/731,638, filed Dec. 9, 2003, entitled "Modular Implantable Medical Device."
U.S. Appl. No. 10/731,869, filed Dec. 9, 2003, entitled "Modular Implantable Medical Device."
"Surgical Process," Animation Screenshots from http://www.cochlearamerica.com/800.asp, 7 pgs.
"Candidates Brochure," http://www.cochlearamerica.com/pdfs/candidatebrochglobal.pdf, 14 pgs.
"Research and Development," http://www.cochlearamericas.com/384.asp, 1 pg.
"The World Leader in cochlear implants—revolutionizing hearing for adults and infants," http://www.cochlear.com, 1 pg.
"Cochlear: innovator of the Nucleus 3 cochlear implant system," http://www.cochlearamericas.com, 1 pg.
"What is a Cochlear Implant," http://www.cochlearamericas.com/What/161.asp, 1 pg.
"ESPrit 3G Speech Processor," http://www.cochlearamericas.com/591.asp, 2 pgs.
"Nucleus 3 System," http://www.cochlearamericas.com/Products/465.asp, 1 pg.
"Internal Components: Nucleus 24 Cochlear Implants," http://www.cochlearamericas.com/374.asp, 1 pg.
"Nucleus 24 Contour," http://www.cochlearamericas.com/568.asp, 2 pgs.
"Nucleus 24 M," http://www.cochlearamericas.com/372.asp, 1 pg.
"Nucleus 24 K," http://www.cochlearamericas.com/371.asp, 1 pg.
"Nucleus 24 Double Array," http://www.cochlearamericas.com/370.asp, 1 pg.
"Nucleus 24 ABI: Auditory Brainstem Implant," http://www.cochlearamericas.com/373.asp, 2 pgs.
"Nucleus Speech Processors," http://www.cochlearamericas.com/629.asp, 1 pg.
"Sprint: body worn speech processor," http://www.cochlearamericas.com/1010.asp, 1 pg.
"Cochlear," http://www.cochlearamericas.com/Recipients/978.asp, 3 pgs.
Answers.com, www.answers.com, defined: discrete components, acessed on Mar. 2, 2007 (2 pages).

* cited by examiner

CONCAVITY OF AN IMPLANTABLE MEDICAL DEVICE

This application claims the benefit of:

1. U.S. Provisional Application entitled "CRANIAL NEUROSTIMULATOR AND METHOD," Ser. No. 60/431,854, filed on Dec. 9, 2002;
2. U.S. Provisional Application entitled "IMPLANTABLE CRANIAL MEDICAL DEVICES AND METHODS," Ser. No. 60/471,262, filed on May 16, 2003;
3. U.S. Provisional Application entitled "IMPLANTABLE CRANIAL MEDICAL DEVICES AND METHODS," Ser. No. 60/503,945, filed on Sep. 20, 2003;
4. U.S. Provisional Application entitled "IMPLANTABLE CRANIAL MEDICAL DEVICES AND METHODS," Ser. No. 60/503,946, filed on Sep. 20, 2003; and
5. U.S. Provisional Application entitled "Thin Neuro Stimulation System, Device and Method," Ser. No. 60/507,857, filed on Oct. 1, 2003.

The entire content of each of these U.S. Provisional Applications is incorporated herein by reference.

The following co-pending and commonly-assigned U.S. Patent Applications, filed on even date herewith, are also incorporated herein by reference in their entirety:

1. U.S. patent application Ser. No. 10/731,869, entitled "MODULAR IMPLANTABLE MEDICAL DEVICE," to Carl D. Wahlstrand et al., and filed on Dec. 9, 2003;
2. U.S. patent application Ser. No. 10/731,868, entitled "IMPLANTATION OF LOW-PROFILE IMPLANTABLE MEDICAL DEVICE," to Ruchika Singhal et al., and filed on Dec. 9, 2003;
3. U.S. patent application Ser. No. 10/731,699, entitled "COUPLING MODULE OF A MODULAR IMPLANTABLE MEDICAL DEVICE," to Darren A. Janzig et al., and filed on Dec. 9, 2003;
4. U.S. patent application Ser. No. 10/730,873, entitled "OVERMOLD FOR A MODULAR IMPLANTABLE MEDICAL DEVICE," to Ruchika Singhal et al., and filed on Dec. 9, 2003, which issued as U.S. Pat. No. 7,242,982 on Jul. 10, 2007;
5. U.S. patent application Ser. No. 10/731,881, entitled "REDUCING RELATIVE INTERMODULE MOTION IN A MODULAR IMPLANTABLE MEDICAL DEVICE," to Carl D. Wahlstrand et al., and filed on Dec. 9, 2003, which issued as U.S. Pat. No. 7,392,089 on Jun. 24, 2008;
6. U.S. patent application Ser. No. 10/730,878, entitled "LEAD CONNECTION MODULE OF A MODULAR IMPLANTABLE MEDICAL DEVICE," to Ruchika Singhal et al., and filed on Dec. 9, 2003;
7. U.S. patent application Ser. No. 10/730,877, entitled "LOW-PROFILE IMPLANTABLE MEDICAL DEVICE," to Darren A. Janzig et al., and filed on Dec. 9, 2003; and
8. U.S. patent application Ser. No. 10/731,638, entitled "MODULAR IMPLANTABLE MEDICAL DEVICE," to Carl D. Wahlstrand et al., and filed on Dec. 9, 2003, which issued as U.S. Pat. No. 7,212,864 on May 1, 2007.

TECHNICAL FIELD

The invention relates to medical devices, and more particularly, to implantable medical devices that deliver therapy to and/or monitor a patient.

BACKGROUND

Depending on the application for which they are implanted in a patient, implantable medical devices (IMDs) may include a variety of electrical and/or mechanical components. Typically, an IMD includes a rigid housing that houses all of its components, which are generally fragile, to protect the components from forces to which they would otherwise be exposed when implanted within the human body. In order to avoid potentially harmful interactions between the components and bodily fluids, e.g., corrosion, IMD housings are typically hermetically sealed. Many IMD housings are fabricated from Titanium because of its desirable rigidity and biocompatibility.

The size and shape of an IMD housing is dependant on the sizes and shapes of the components of the IMD. Large components common to most IMDs include a battery, a telemetry coil, and a circuit board that carries digital circuits, e.g., integrated circuit chips and/or a microprocessor, and analog circuit components. Attempts have been made to reduce the size of the IMD housing by reducing the size of these components, changing the shape of these components, and organizing these components within the IMD housing to avoid empty space within the housing. Despite these efforts to reduce the size of IMD housings, the size, shape and rigidity of IMD housings still greatly limits the locations within the human body where an IMD can be practically implanted.

Due to these limitations, an IMD is typically implanted within the abdomen, upper pectoral region, or subclavicular region of a patient. Leads or catheters must be used in order to deliver therapy or monitor a physiological parameter at a location of the body other than where the IMD is implanted. Implantation and positioning of leads and catheters can be difficult and time-consuming from the perspective of a surgeon, particularly where the IMD is located a significant distance from the treatment or monitoring site. Moreover, the increased surgical time, increased surgical trauma, and increased amount of implanted material associated with the use of leads and catheters can increase the risk to the patient of complications associated with the implantation of an IMD.

For example, IMDs that are used to treat or monitor the brain, e.g., to deliver deep brain stimulation (DBS) therapy, are implanted some distance away from the brain, e.g., within the subclavicular region of patients. The long leads that connect the implantable medical device to electrodes implanted within the brain require tunneling under the scalp and the skin of the neck, thereby requiring increased surgery and a prolonged amount of time under general anesthesia during the implant procedure, as well as increased recovery time. In some cases, tunneling the leads under the scalp and skin of the neck requires an additional surgical procedure under general anesthesia. The lengthy tract along the leads is more susceptible to infection, and the leads can erode the overlying scalp, forcing removal so that the scalp can heal. Further, the long leads running under the scalp and through the neck are more susceptible to fracture due to torsional and other forces caused by normal head and neck movements.

SUMMARY

In general, the invention is directed to a concave implantable medical device. In particular, at least one surface of an implantable medical device is concave along at least one axis such that it substantially conforms to a surface within a patient, such as the cranium, when it is implanted on that surface. In some embodiments, the surface of the implantable medical device substantially conforms to an arc with a radius that is between 4.5 and 9.5 centimeters, and is preferably approximately equal to 7 centimeters.

In some embodiments, the implantable medical device comprises a plurality of interconnected modules, and an overmold that at least partially encapsulates each of the modules. In such embodiments, at least one surface of the overmold is itself concave along at least one axis. The overmold may be flexible.

Further, each of the modules of such an implantable medical device may comprise a housing, and at least one surface of at least one of the housings may be concave along at least one axis. Both of the overmold and housing surfaces may substantially conform to an arc with a radius that is between 4.5 and 9.5 centimeters, and is preferably approximately equal to 7 centimeters. In some embodiments, a second surface of the overmold and/or the housing, e.g., a top surface, is convex such that it also substantially conforms to the arc. In exemplary embodiments, the implantable medical device is implanted on the cranium of a patient beneath the scalp, and is a neurostimulator that delivers stimulation to the brain of the patient.

In one embodiment, the invention is directed to an implantable medical device that includes a plurality of interconnected modules, each of the modules comprising a housing. The implantable medical device also includes an overmold that at least partially encapsulates each of the modules. A surface of the overmold is concave along at least one axis.

In another embodiment, the invention is directed to an implantable medical device that includes a housing. The housing includes a surface that is proximate to a cranium of a patient when the implantable medical device is implanted on the cranium. The surface of at least one of the modules is concave along at least one axis such that the surface conforms substantially to an arc. A radius of the arc is within a range from 4.5 to 9.5 centimeters.

The invention may be capable of providing one or more advantages. For example, the concavity of an implantable medical device according to the invention can enable the implantable medical device to be implanted at locations within the human body for which implantation of conventional implantable medical devices is deemed undesirable. In particular, a concave housing surface and/or overmold surface can enable an implantable medical device which delivers treatment to the brain of a patient, such as implantable neurostimulator, to be implanted on the cranium of a patient rather then more remotely from the brain, such as within an subclavicular region of the patient. Consequently, the problems associated with the use of long leads needed to allow a remotely implanted medical device to access the brain may be diminished or avoided.

Further, the combination of a concave housing bottom surface and convex housing top surface, and/or the combination of a concave overmold bottom surface and a convex overmold top surface may make the implantable device more comfortable, less noticeable, e.g., more cosmetically appealing, and more clinically acceptable when implanted on the cranium beneath the scalp of the patient. For example, the combination of a concave overmold bottom surface and a convex overmold top surface may make the implantable medical device more clinically acceptable by resulting in tapered overmold edges that reduce the likelihood of skin erosion on the scalp over the device.

The details of one or more embodiments of the invention are set forth in the accompanying drawings and the description below. Other embodiments of the invention will be apparent from the description and drawings, and from the claims.

DETAILED DESCRIPTION

Figure 1:
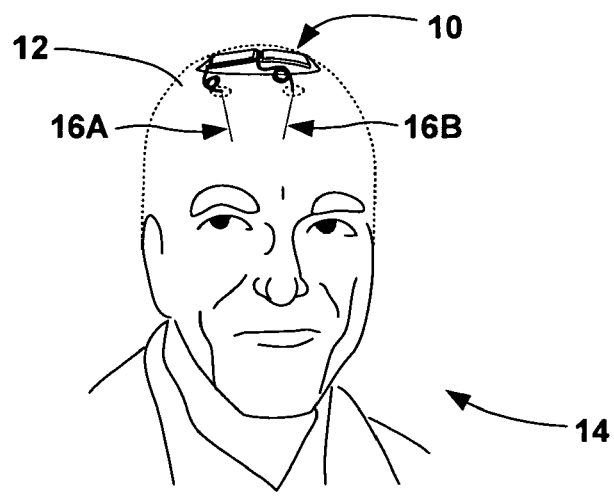
FIG. 1 is a conceptual diagram illustrating an example modular implantable medical device implanted on the cranium of a patient.

FIG. 1 is a conceptual diagram illustrating an example modular implantable medical device (IMD) 10 implanted on the cranium 12 of a patient 14. As will be described in greater detail below, IMD 10 comprises a plurality of separately housed and interconnected modules. Further, modular IMD 10 is concave. In particular, at least one surface of an overmold of modular IMD 10 that at least partially encapsulates the modules thereof is concave, and, in some embodiments, at least one surface of one or more of the modules themselves is concave.

By distributing components of IMD 10 amongst modules rather than including them within a single, rigid housing, the implantable medical device may be shaped and configured for implantation at locations within patient 14, such as on cranium 12, for which implantation of conventional IMDs is deemed undesirable. Further, the overmold and/or modules of modular IM 10 may be concave such that they substantially conform to cranium 12. This concavity of modular IMD 10 contributes to the ability of modular IMD 10 to be implanted on cranium 12 rather then more remotely from the brain of patient 14, thus avoiding problems associated with the use of long leads needed to allow a remotely implanted conventional IMDs to access the brain. These problems include the requirement of tunneling under the scalp and the skin of the neck, increased surgery and recovery time, an additional procedure under general anesthesia, risk of infection or skin erosion along the track through which the leads are tunneled, and risk of lead fracture due to torsional and other forces caused by normal head and neck movements.

The flexibility of the interconnection between modules of IMD 10 may allow. multiples degrees of freedom of movement between the modules, which in turn may allow the implantable medical device to conform to areas such as the surface of cranium 12. In some embodiments, the overmold may be flexible, and the flexible overmold and flexible interconnection of modules may allow modular IMD 10 to be manipulated during implantation to substantially conform to cranium 12, allowing an already concave IMD 10 to be custom shaped to fit the cranium of a particular patient. Further, combinations of concave and convex housing surfaces and/or overmold surfaces may make the implantable device more comfortable, less noticeable, e.g., more cosmetically appealing, and more clinically acceptable when implanted on the cranium beneath the scalp of the patient.

In the illustrated example, modular IMD 10 is coupled to two leads 16A and 16B (collectively "leads 16") that extend through holes within cranium 12, and into the brain of patient 14. In exemplary embodiments, each of leads 16 carries a plurality of electrodes, and IMD 10 delivers stimulation to the brain of patient 14 via the electrodes. Modular IMD 10 may be coupled to any number of leads 16, and in some embodiments is not coupled to any leads 16.

Figure 2:
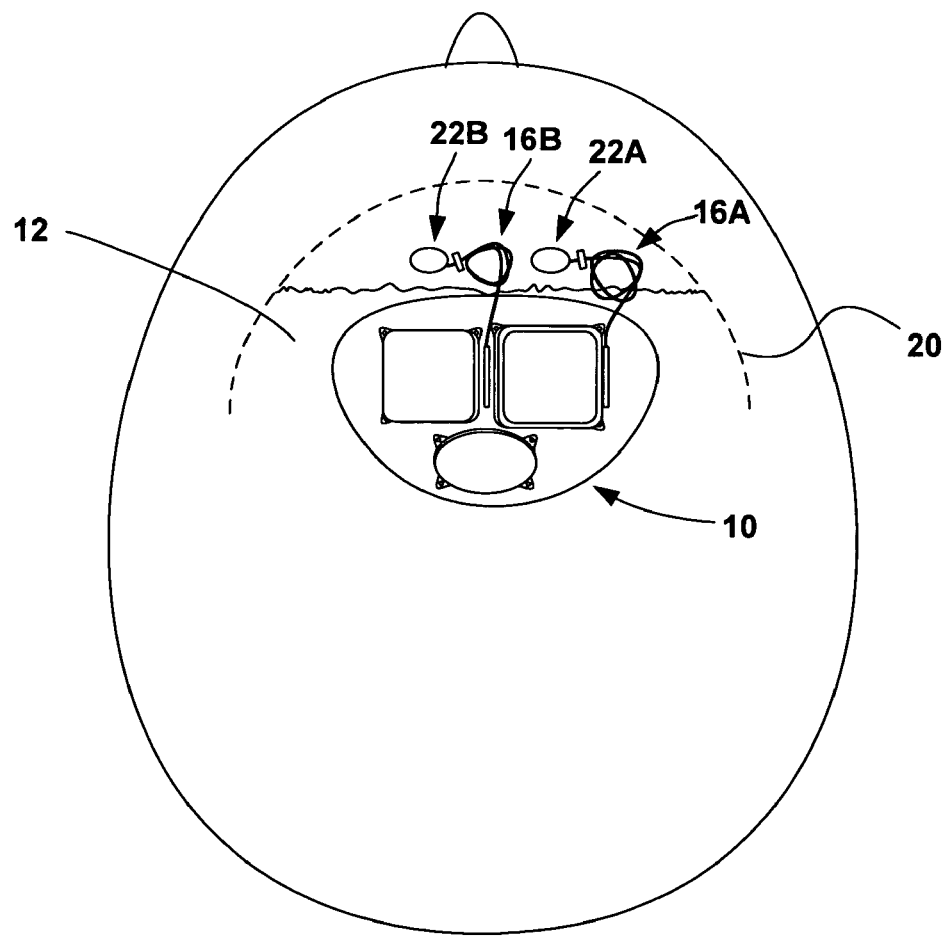
FIG. 2 is a top-view diagram further illustrating the modular implantable medical device of FIG. 1 implanted on the cranium of the patient.

FIG. 2 is a top-view diagram further illustrating modular IMD 10 implanted on cranium 12 of the patient 14. In order to implant modular IMD 10 on cranium 12, an incision 20 is made through the scalp of patient 14, and a resulting flap of skin is pulled back to expose the desired area of cranium 12. The incision may, as shown in FIG. 2, be generally shaped like a "C." Such an incision is commonly referred to as a "C-flap" incision.

Holes 22A and 22B (collectively "holes 22") are drilled through cranium 12, and leads 16 are inserted through holes 22 and into the brain of patient 14. Caps may be placed over holes 22 as is known in the art. Leads 16 are connected to modular IMD 10, either directly or via a lead extension, and modular IMD 10 is placed at least partially within a pocket formed using a hand or a tool beneath the scalp behind holes 22.

Once positioned as desired on cranium 12 within the pocket, modular IMD 10 may then be fixed to cranium 12 using an attachment mechanism such as bone screws. The skin flap may be closed over modular IMD 10, and the incision may be stapled or sutured. The location on cranium 12 at which IMD 10 is illustrated as implanted in FIG. 2 is merely exemplary, and IMD 10 can be implanted anywhere on the surface of cranium 12. Further details regarding exemplary techniques for implanting IMD 10 on the cranium may be found in a commonly-assigned U.S. patent application Ser. No. 10/731,868, entitled "IMPLANTATION OF LOW-PROFILE IMPLANTABLE MEDICAL DEVICE."

Because of the flexibility provided by interconnect members and/or an overmold of modular IMD 10, the IMD may be manipulated during implantation such that it conforms to cranium 12. For example, in some embodiments a clinician can manipulate modular IMD 10 into conformance with cranium 12 while IMD 10 is on cranium 12 and fix modular IMD 10 into place using bone screws or the like. In other embodiments, the clinician may manipulate modular IMD 10 into conformance with cranium 12 with IMD 10 on and/or off of cranium 12, and IMD 10 may substantially retain the form into which it is manipulated.

As mentioned above, modular IMD 10 may deliver stimulation to the brain of patient 14 to, for example, provide deep brain stimulation (DBS) therapy, or to stimulate the cortex of the brain. Cortical stimulation may involve stimulation of the motor cortex. Modular IMD 10 may be used to treat any nervous system disorder including, but not limited to, epilepsy, pain, psychological disorders including mood and anxiety disorders, movement disorders (MVD), such as, but not limited to, essential tremor, Parkinson's disease, and neurodegenerative disorders.

However, modular IMD 10 is not limited to delivery of stimulation to the brain of patient, and may be employed with leads 16 deployed anywhere in the head or neck including, for example, leads deployed on or near the surface of the skull, leads deployed beneath the skull such as near or on the dura mater, leads placed adjacent cranial or other nerves in the neck or head, or leads placed directly on the surface of the brain. Moreover, modular IMD 10 is not limited to implantation on cranium 12. Indeed, modular IMD 10 may be implanted anywhere within patient 14, and may be made suitably concave for implantation at any location. For example, modular IMD 10 can be implanted within the neck of patient 14, and deliver stimulation to the vagus nerve or the cervical region of the spinal cord.

Modular IMD 10 may alternatively be implanted within a pectoral region or the abdomen of patient 14 to act as a diaphragmatic pacer, or to provide any of the monitoring and therapy delivery functions known in the art to be associated with cardiac pacemakers. Further, modular IMD 10 may be implanted in the upper buttock region and deliver spinal cord, urological or gastrological stimulation therapy, or may be configured to be implanted within the periphery, e.g., limbs, of patient 14 for delivery of stimulation to the muscles and/or peripheral nervous system of patient 14. As is the case with cranium 12, the modularity of IMD 10 may enable implantation at some of these example locations for which implantation of conventional IMDs is generally deemed undesirable.

Modular IMD 10 is not limited to embodiments that deliver stimulation. For example, in some embodiments modular IMD 10 may additionally or alternatively monitor one or more physiological parameters and/or the activity of patient 14, and may include sensors for these purposes. Where a therapy is delivered, modular IMD 10 may operate in an open loop mode (also referred to as non-responsive operation), or in a closed loop mode (also referred to as responsive). Modular IMD 10 may also provide warnings based on the monitoring.

As discussed above, the ability of a modular IMD 10 according to the invention to be implanted close to a region within patient 14 to be monitored enables the use of shorter leads 16. Shorter leads 16 may advantageously improve the accuracy of such sensors by reducing noise attributable to leads 16. Shorter leads 16 may also advantageously reduce the negative affects of imaging techniques such as magnetic resonance imaging "MRI" on a person implanted with IMD 10.

Further, in some embodiments modular IMD 10 can additionally or alternatively deliver a therapeutic agent to patient 14, such as a pharmaceutical, biological, or genetic agent. Modular IMD 10 may be coupled to a catheter, and may include a pump to deliver the therapeutic agent via the catheter.

Figure 3:
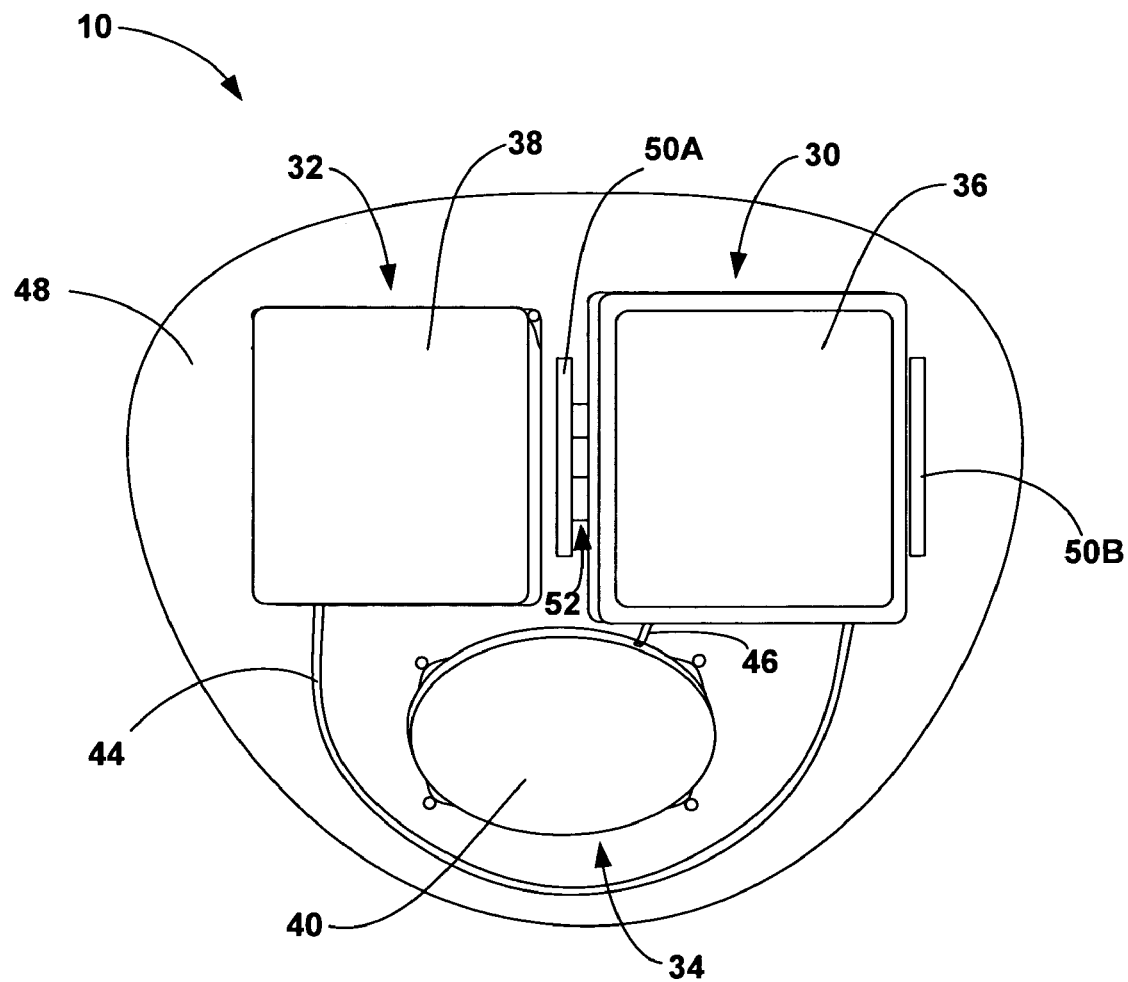
FIG. 3 is a top-view diagram further illustrating the modular implantable medical device of FIG. 1.

FIG. 3 is a top-view diagram further illustrating modular IMD 10. In the illustrated embodiment, modular IMD 10 includes three modules: a control module 30, a power source module 32, and a recharge module 34. As shown in FIG. 3, modules 30, 32 and 34 include separate housings 36, 38 and 40, respectively.

Control module 30 includes control electronics within the housing, e.g., electronics that control the monitoring and/or therapy delivery functions of modular IMD 10, such as a microprocessor. Control module 30 may also include circuits for telemetry communication with external programmers or other devices within the housing. Housing 36 of control module 30 may be hermetic in order to protect the control electronics therein, and in exemplary embodiments is formed of a rigid material, such as titanium, stainless steel, or a ceramic.

In exemplary embodiments, housing 36 is a low-profile, concave housing, and techniques for arranging components of control module 30 to enable such a low-profile, concave housing are described in greater detail in a commonly-assigned U.S. patent application Ser. No. 10/730,877, entitled "LOW-PROFILE IMPLANTABLE MEDICAL DEVICE."

Figure 4:
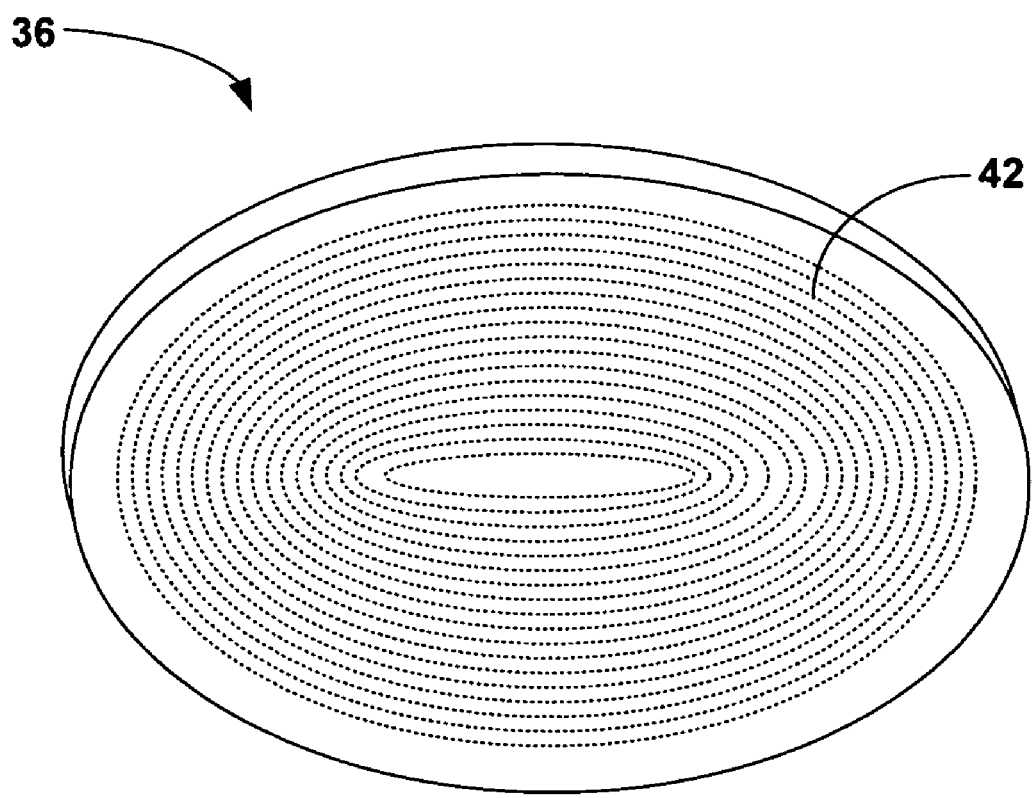
FIG. 4 is top-view diagram illustrating a recharge module of the modular implantable medical device of FIG. 1.

Power source module 32 includes a power source within housing 38. The power source provides power for components of other modules, such as the control electronics within control module 30. The power source may be any power source suitable for use within an IMD, such as one or more batteries, capacitors, solar cells, fuel cells, nuclear cells, or any combination thereof. In an exemplary embodiment, the power source comprises a rechargeable Lithium Ion battery, which may have a thin wound coil construction, or a foil pack or other non-coiled construction to more easily fit within housing 38 which may be concave and less than 5 millimeters thick with an approximately one square inch surface area. Housing 38 may be hermetic, and may be formed of titanium, stainless steel, or a ceramic. Power source module 32 may include an insulator within housing 38 to isolate housing 38 from the power source.

Where the power source includes a rechargeable power, such as a rechargeable battery and/or a capacitor, modular IMD 10 may include recharge module 34. As shown in FIG. 4, recharge module 34 includes a recharge coil 42 within housing 40. Recharge coil 42 inductively receives energy from an external recharging unit (not illustrated) through the skin of patient 14 to recharge the power source. Recharge coil 42 may be formed of windings of copper or another highly conductive material. Both recharge coil 42 and housing 40 may be made concave. Housing 40 need not be hermetic, and may be formed of materials such as silicone, polymers and ceramics.

Housings 36, 38 and 40 may have any shape, including the round, coin shape and rectangular shapes with rounded edges illustrated in FIG. 3. Further, the surface of one or more of housings 36, 38 and 40 proximate to cranium 12 when implanted may be concave along at least one axis, and preferably two axes. The concavity of housings 36, 38 and 40 will be described in greater detail below with reference to FIGS. 10A and 10B.

Modules 30, 32 and 34 can be configured in a variety of ways, and the configuration illustrated in FIG. 3 is merely exemplary. Additional exemplary configurations are described wit reference FIGS. 7A and 7B below. Further, modular IMD 10 can include any number of modules, and may include other types of modules instead of or in addition to a power source module 32 and a recharge module 34. For example, modular IMD 10 can include additional power source modules, modules that include additional memory that is accessible by the control electronics within control module 30, modules that include reservoirs for storing therapeutic agents and pumps for delivering therapeutic agents to patient 14, and modules that include sensors sensing physiological parameters, such as pressures or blood flows, or the activity level of patient 12. Each such module may include a surface that is concave along at least one axis. Further details regarding additional modules for and/or configurations of modules of a modular IMD may be found in a commonly-assigned U.S. patent application Ser. No. 10/731,869, entitled "MODULAR IMPLANTABLE MEDICAL DEVICE."

Power source module 32 is coupled to control module 30 by a flexible interconnect member 44, which encloses a conductor that allows transmission of energy from the power source of power source module 32 to components such as the control electronics within control module 30. In embodiments where energy is transferred via a DC voltage on the conductor, it may be necessary to make flexible interconnect member 44 hermetic. In embodiments in which flexible interconnect member 44 is hermetic, flexible interconnect member 44 may be made of titanium or stainless steel. In embodiments where energy is transferred via a charged-balanced voltage on the conductor, such as an AC voltage, flexible interconnect member 44 need not be hermetic, and may be made of any material including silicone or various polymers.

In the illustrated embodiment, the control electronics of control module 30 regulates the recharging and discharging of the power source within power source module 32. Consequently, as shown in FIG. 3, recharge module 34 is coupled to control module 30 by a flexible interconnect member 46 that encloses a conductor that allows transmission of energy inductively received by coil 42 to control module 30. Because the energy is transferred on the conductor via a charged-balanced voltage, flexible interconnect member 46 need not be hermetic, and may be made of any material including titanium, stainless steel, ceramics, silicone or various polymers.

Interconnect members 44 and 46 are flexible. In some embodiments, as indicated above, interconnect members 44 and 46 are made of a flexible material such as silicone or a flexible polymer. In embodiments where flexible member 44 is hermetic and made of substantially less flexible material, such as titanium or stainless steel, the flexibility of interconnect member 44 is provided by the configuration and/or construction of flexible interconnect member 44.

Interconnect member 44 is flexible in a plurality of directions to provide modules 30 and 32 with multiple degrees of freedom of motion with respect to each other. In exemplary embodiments, interconnect member 44 provides at least three degrees of motion, and the degrees of motion provided include rotational motion. Further details regarding the configuration and/or construction of interconnect member 44 to provide such flexibility may be round in a commonly assigned U.S. patent application Ser. No. 10/731,699, entitled "COUPLING MODULE OF A MODULAR IMPLANTABLE MEDICAL DEVICE."

As shown in FIG. 3. modular IMD 10 includes an overmold 48, which may be flexible. In the illustrated embodiment, overmold 48 at least partially encapsulates each of housings 36, 38 and 40. Further, as illustrated in FIG. 3. housings 36, 38 and 40 may be horizontally distributed at respective locations of overmold 48. Overmold 48 integrates modules 30, 32 and 34 into a desired form factor, but where flexible, allows relative intermodule motion. In some embodiments, a flexible overmold 48 incorporates mechanical features to restrict intermodule motion to certain directions or within certain ranges. A flexible overmold 48 may be made from silicone, and is some embodiments may be made from two or more materials of differing flexibility, such as silicone and a polyurethane. An exemplary polyurethane for this purpose is Tecothane®, which is commercially available from Hermedics Polymer Products, Wilmington, Mass. Use of the term "overmold" herein is not intend to limit the invention to embodiments in which overmold 48 is a molded structure. Overmold 48 may be a molded structure, or may be a structure formed by any process.

Overmold 48 can be shaped to contour to cranium 12, e.g., may be concave along at least one axis, and may be contoured at its edges to prevent skin erosion on the scalp of patient 14. The flexibility and shape, e.g., concavity, of overmold 48 may improve the comfort and cosmetic appearance of modular IMD 10 under the scalp. Further details regarding the overmold and techniques for restricting intermodular motion in a modular IMD 10 may be found in a commonly-assigned U.S. patent application Ser. No. 10/730,873, entitled "OVERMOLD FOR A MODULAR IMPLANTABLE MEDICAL DEVICE," now issued as U.S. Pat. No. 7,24,982, and a commonly-assigned U.S. patent application Ser. No. 10/731,881, entitled "REDUCING RELATIVE INTERMODULE MOTION IN A MODULAR IMPLANTABLE MEDICAL DEVICE," now issued as U.S. Pat. No. 7,392,0894.

In the illustrated embodiment, modular IMD 10 also includes lead connector modules 50A and 50B (collectively "lead connector modules 50") formed within overmold 48 to receive leads 16 or lead extensions coupled to leads 16. Conductors 52 extend from lead connector modules 50 to hermetic feedthroughs (not illustrated) within housing 36 of control module 30. Lead connector modules 50 may be formed anywhere within overmold 48. In embodiments where overmold 48 includes both a rigid material and flexible material, the rigid material may form at least part of lead connector modules 50 to secure leads 16 or lead extensions, and to protect conductors 52 from damage that may result from flexing within overmold 48.

Figure 5:
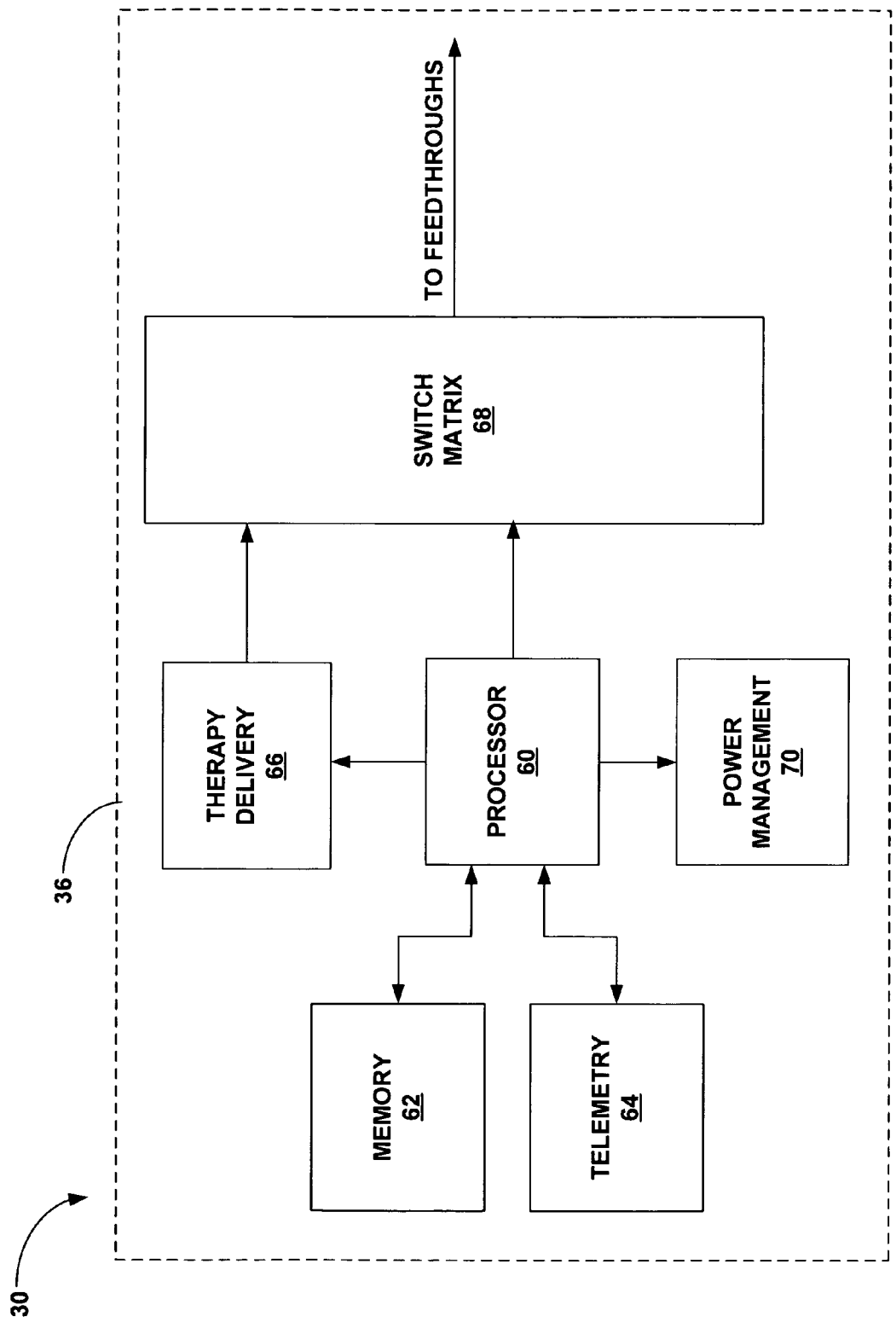
FIG. 5 is a block diagram illustrating a control module of the modular implantable medical device of FIG. 1.

FIG. 5 is a block diagram illustrating control module 30 of modular IMD 10. As described above, control module 30 includes control electronics that control the functioning of modular IMD 10 within housing 36. The control electronics include a processor 60, which may take the form of a microprocessor, digital signal processor (DSP), application specific integrated circuit (ASIC), field-programmable gate array (FPGA), or other logic circuitry.

Control module 30 also includes a memory 62, such as a read-only memory (ROM), random access memory (RAM), electronically-erasable programmable ROM (EEPROM), flash memory, or the like. Memory 62 may store program instructions that may be executed by processor 60 and thereby control the functioning of modular IMD 10. Processor 60 may also store data colleted during treatment and/or monitoring of patient 14 within memory 62.

In some embodiments, control module 30 includes telemetry circuitry 64, which enables processor 60 to communicate with other devices such, as an external programming device via radio-frequency communication. Telemetry circuitry 64 may include a telemetry coil (not illustrated), which may be fabricated of windings of copper or another highly conductive material. The configuration and location of telemetry coil within housing 36 may be dictated by the available space within housing 36 and the communication requirements of telemetry circuitry 64. Further detail regarding the configuration and location of the telemetry coil may be found in a commonly-assigned U.S. patent application Ser. No. 10/720,877, entitled "LOW-PROFILE IMPLANTABLE MEDICAL DEVICE."

In some embodiments modular IMD 10 delivers electrical stimulation, and more particularly, control module 30 includes therapy delivery circuitry 66 within housing 36 that generates electrical stimulation. In exemplary embodiments, therapy delivery circuitry 66 comprises circuits for the generation of electrical stimulation in the form of pulses, such as capacitors and switches. In embodiments in which modular IMD 10 is a neurostimulator coupled to leads 16 that include a plurality of electrodes, therapy delivery circuitry 66 may deliver the pulses to a switch matrix 68, which comprises an array of switches. In such embodiments, processor 60 interacts with switch matrix 68 to select electrodes for delivery of generated stimulation pulses. Based on the selections made by processor 60, switch matrix 68 delivers the pulses to conductors that pass through feedthroughs in housing 36 and to electrical contacts on leads 16 that are electrically coupled to the desired electrodes carried by leads 16.

The illustrated components of control module 30 receive energy from the power source within power source module 32 via interconnect member 44 (FIG. 3). In some embodiments in which the power source is rechargeable, control module 30 receives energy inductively captured by recharge module 34 via interconnect member 46, and includes power management circuitry 70 that controls the recharging and discharging of the power source. Power management circuitry 70 may ensure that the power source is not overcharged, over-discharged or harmed. In some embodiments, power management circuitry 70 includes circuits to measure voltages, currents or temperatures associated with the power source, or rates of change of these parameters, and controls recharging and discharging according to the measured values. Power management circuitry 70 may also include circuits, such as rectifier circuits, for converting AC voltages provided by recharge coil 42 (FIG. 4) into DC voltages for recharging the power source.

Figure 6:
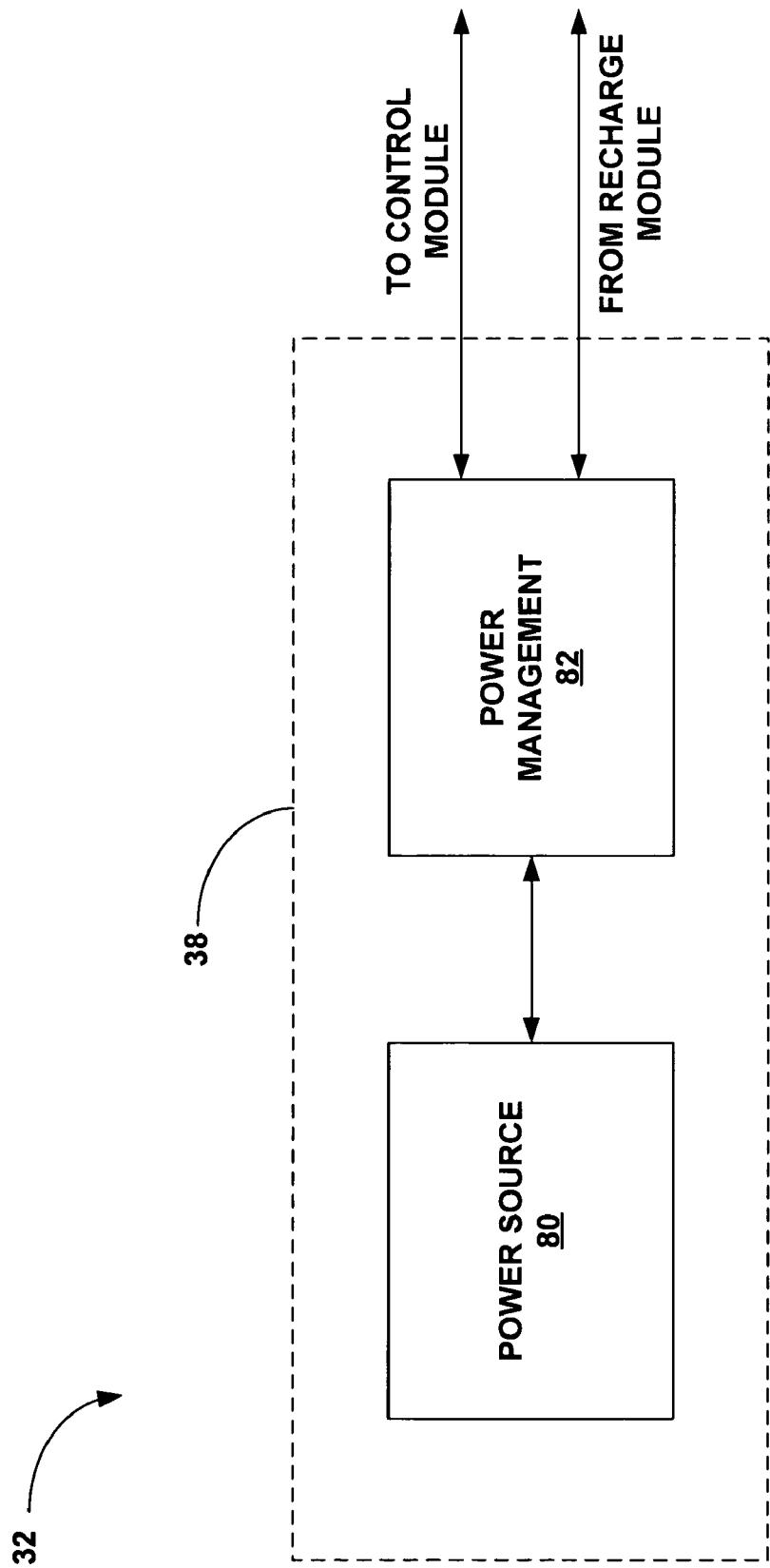
FIG. 6 is a block diagram illustrating a power source module of the modular implantable medical device of FIG. 1.

FIG. 6 is a block diagram illustrating power source module 32 of modular IMD 10. Power source module 32 includes a rechargeable power source 80 within housing 38, which may include a battery and/or a capacitor. Further, in some embodiments, power source module 32 includes power management circuitry 82.

Although not illustrated herein, in some embodiments flexible interconnect member 44 directly connects recharge module 34 to power source module 32. In such embodiments, management circuitry 82 controls the recharging and discharging of power source 80 instead of, or in addition to power management circuit 70 within control module 30. As described above with reference to power management circuitry 70 illustrated in FIG. 5, power management circuitry 82 may ensure that power source 80 is not overcharged, over-discharged, or harmed. In some embodiments, power management circuitry 82 includes circuits to measure voltages, currents or temperatures associated with power source 80, or rates of change of these parameters, and controls recharging and discharging of power source 80 according to the measured values.

Power management circuitry 82 may also include circuits, such as rectifier circuits, for converting AC voltages provided by recharge coil 42 (FIG. 4) into DC voltages for recharging power source 80. In some embodiments in which interconnect member 44 is non-hermetic, power management circuitry 82 includes modulating circuits, i.e., circuits that enable power management circuitry 82 to deliver energy to control module 30 in the form of charge-balanced, e.g., AC, voltages on a conductor. In such embodiments, control module 30 includes circuits, such as rectifier circuits, to convert the change-balanced voltages to DC voltages for use by components of control module 30.

Figure 7B:
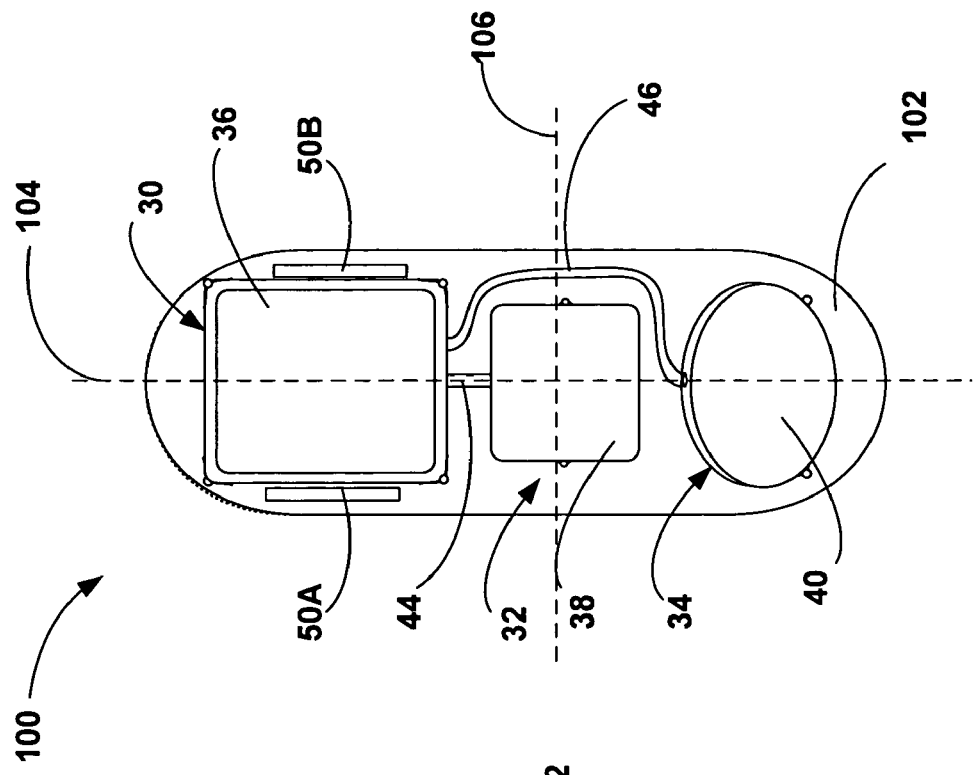
FIGS. 7A and 7B are top-view diagrams illustrating other example modular implantable medical devices.
Figure 7A:
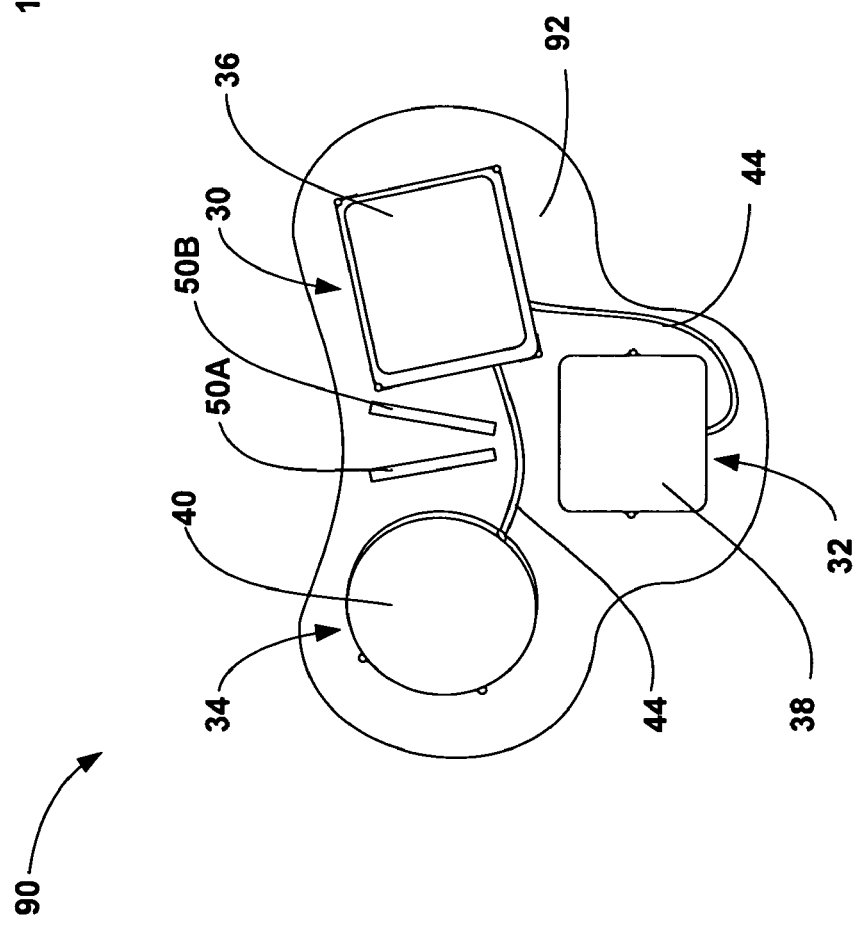

FIGS. 7A and 7B are top-view diagrams illustrating other example modular IMDs 90 and 100, respectively. More particularly, FIGS. 7A and 7B illustrate modular IMDs 90 and 100 that include alternative arrangements of modules 30, 32 and 34, flexible interconnect members 44 and 46, and lead connection modules 50. Further, FIGS. 7A and 7B illustrate alternatively shaped overmolds 92 and 102, respectively, that at least partially encapsulate modules 30, 32 and 34 of modular IMDs 90 and 100. As illustrated in FIGS. 7A and 7B, each IMDs 90 and 100 include the housings of modules 30, 32 and 34 horizontally distributed at respective locations of overmolds 92 and 102.

FIGS. 3 and 7A illustrate substantially triangular configurations of modules 30, 32 and 34 within modular IMDs 10 and 90, respectively. Further, overmolds 48 and 92 of IMDs 10 and 90 have substantially triangular shapes. Substantially triangular configurations of modules 30, 32 and 34 and substantially triangularly shaped overmolds such as overmolds 48 and 92 may be preferred for some implantations, such as that described with reference to FIG. 2, in order to reduce the depth of the pocket formed under the scalp of patient 14. Reduced pocket depth may allow for easier explant of modular IMDs 10 and 90 in the event explant is required. However, other configurations are possible, such as the substantially linear configuration of modules 30, 32 and 34 within modular IMD 100 illustrated FIG. 7B.

Figure 8A:
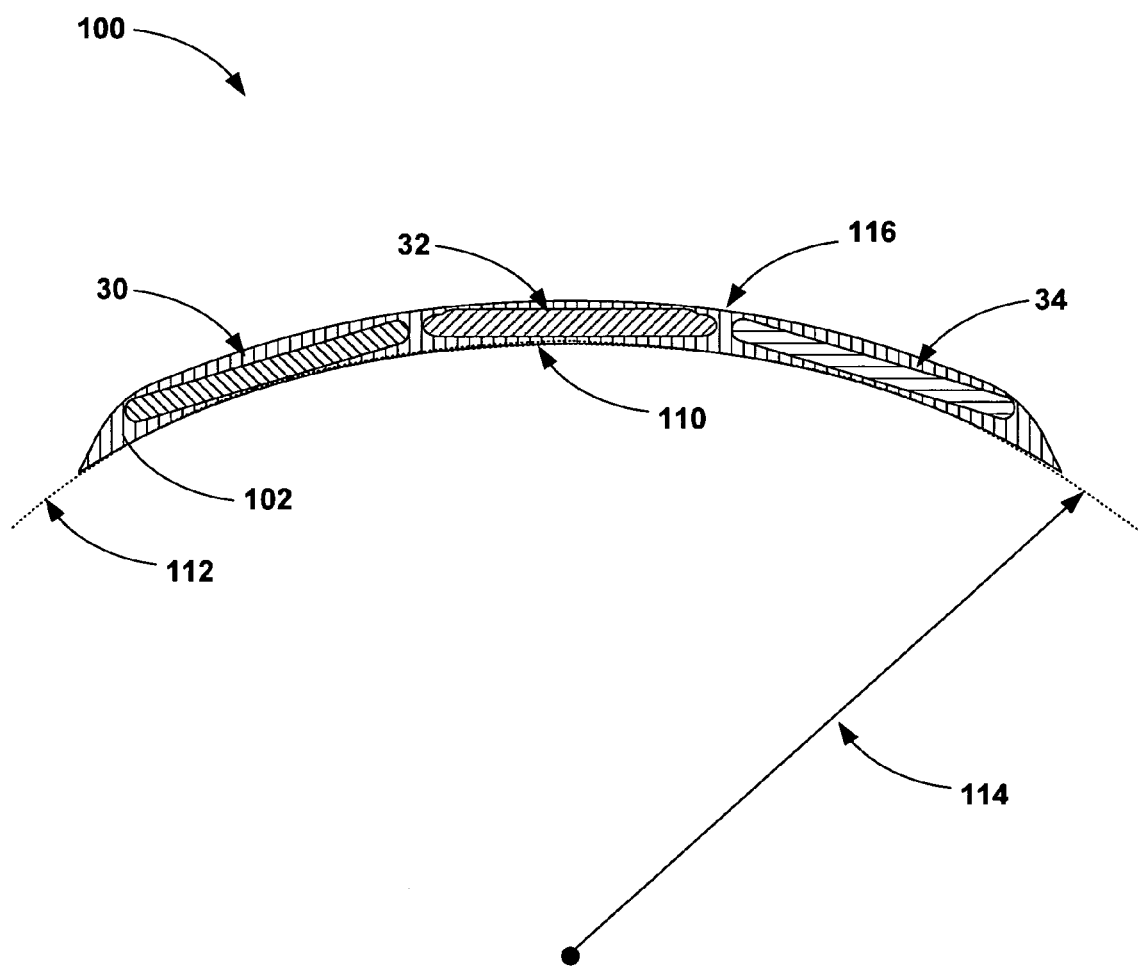
FIGS. 8A and 8B are cross-sectional diagrams of the modular implantable medical device of FIG. 7B illustrating the concavity of the modular implantable medical device of FIG. 7B.
Figure 8B:
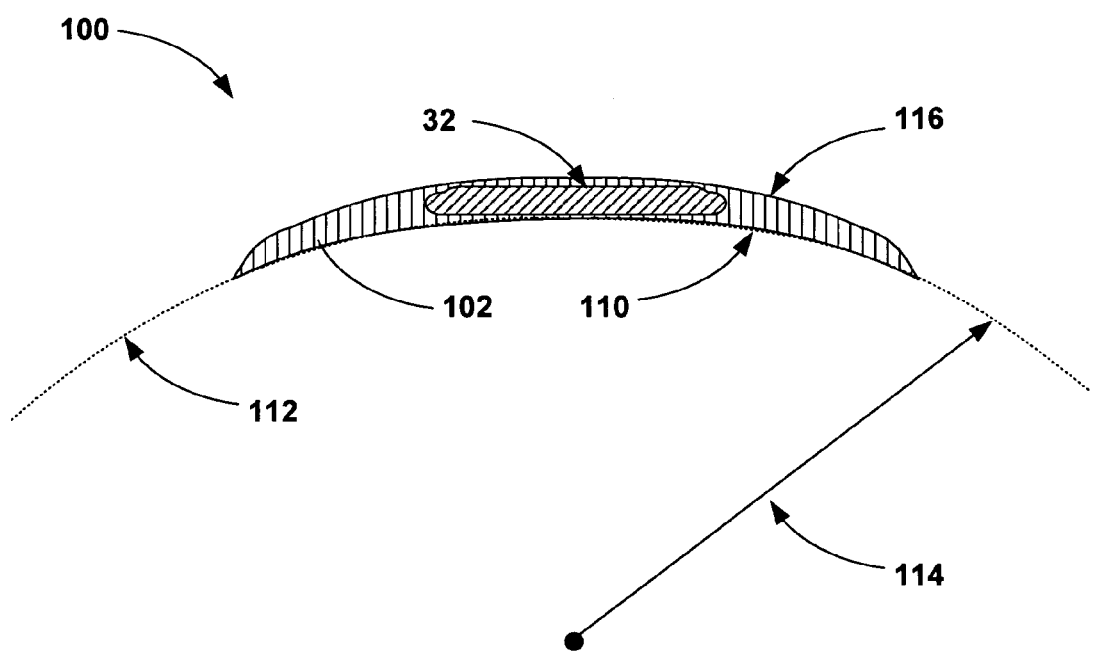

FIGS. 8A and 8B are cross-sectional diagrams of modular IMD 100 illustrating the concavity of modular IMD 100. In particular, FIGS. 8A and 8B illustrate the concavity of overmold 102 of modular IMD 100. The cross-sections are taken along axes 104 and 106 illustrated in FIG. 7B. In the example illustrated in FIGS. 8A and 8B, overmold 102 is concave both of axes 104 and 106.

Overmold 102 may be concave such that it substantially conforms to cranium 102. Human craniums have a radius of curvature that is generally between 4.5 and 9.5 centimeters, and an average radius of curvature is approximately 7 centimeters. Consequently, as illustrated in FIGS. 8A and 8B, surface 110 of overmold 102 is concave such that overmold 102 substantially conforms to an arc 112 with a radius 114 that is between 4.5 and 9.5 centimeters, and is preferably approximately equal to 7 centimeters. Surface 110 is a "bottom" surface of overmold 102 that is proximate to cranium 12 when IMD 100 is implanted thereon. A "top" surface 116 that is distal from cranium 12 when IMD 100 is implanted thereon may be convex as shown in FIGS. 8A and 8B, and may also substantially conform to arc 112.

Although overmold concavity is illustrated with respect to linearly configured modular IMD 100 and its overmold 102, it is understood that modular IMDs with any configuration of the modules therein and any overmold shape may be concave as described with reference to modular IMD 100. For example, overmolds 48 and 92 of modular IMDs 10 and 90 depicted in FIGS. 3 and 7A may be concave as described with reference to modular IMD 100. Further, although overmold 102 is depicted as having a smoothly curving surfaces 110 and 116, it is understood that overmold surfaces that comprise two or more flat surfaces meeting at angles may be concave such that they substantially conform to a cranium and/or an arc as described herein.

Figure 9A:
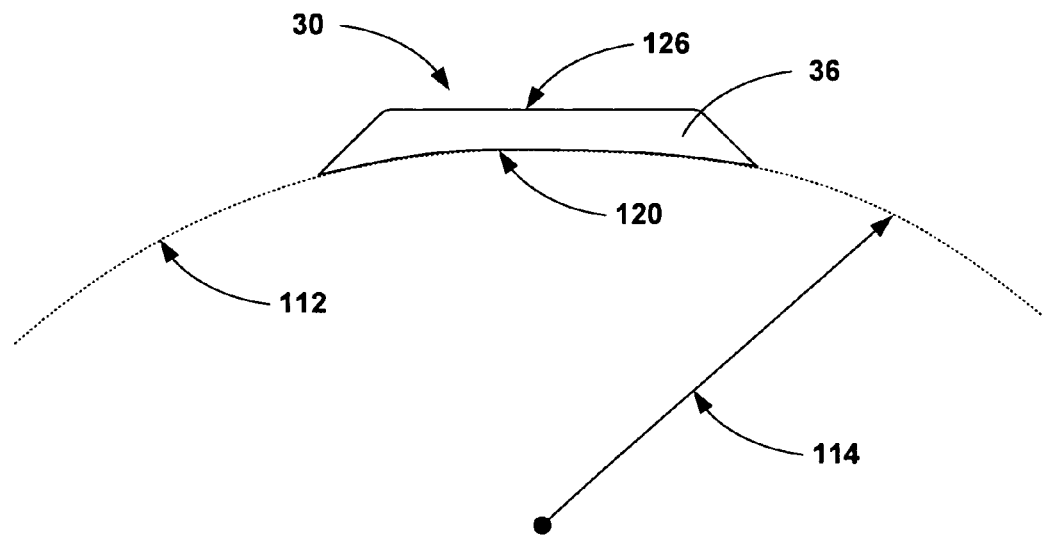
FIGS. 9A and 9B are cross-sectional diagrams of a module of the modular implantable medical device of FIG. 7B illustrating the concavity of the module.
Figure 9B:
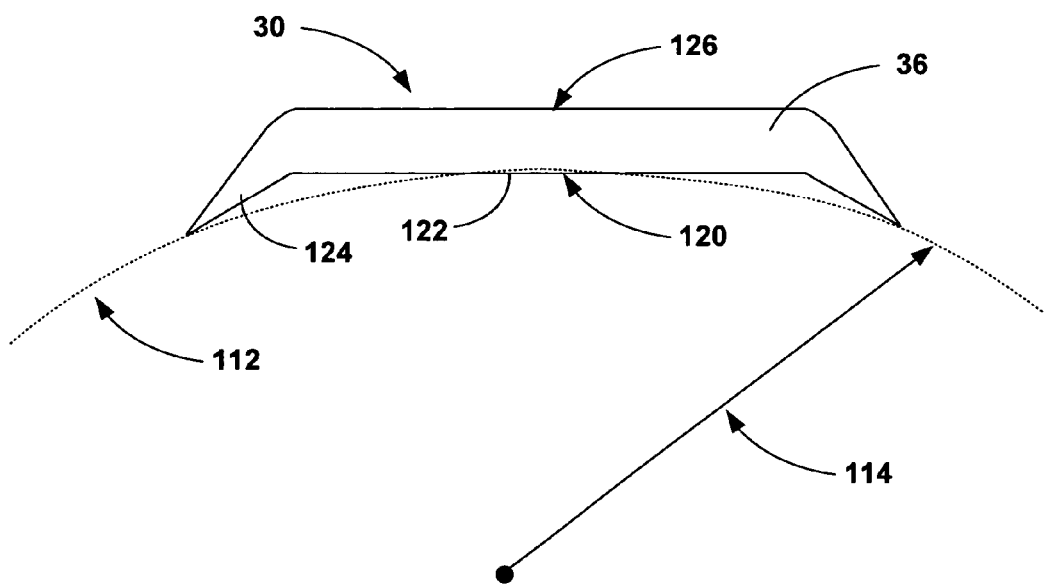

FIGS. 9A and 9B are cross-sectional diagrams of control module 30 illustrating the concavity of housing 36 of control module 30. FIGS. 9A and 9B illustrate different configurations of housing 36. Specifically, FIG. 9A illustrates housing 36 in an embodiment in which a surface 120 that would be proximate to cranium 12 when modular IMD 100 is implanted thereon is smoothly curved. FIG. 9B on the other hand, illustrates housing 36 in an embodiment where surface 120 includes flat portions that interface at an angle in order to achieve substantial concavity, and in particular a central portion 122 and taper portion 124. In both embodiments, surface 120 substantially conforms to arc 112 with a radius 114.

The examples of FIGS. 9A and 9B is merely exemplary, and surface 120 may include any number of portions, which may be flat or have varying radii of curvature, so long as surface 120 is concave as described herein. In some embodiments, a "top" surface 126 that is distal from cranium 12 when IMD 100 is implanted thereon may be convex as shown in FIGS. 9A and 9B, and may also substantially conform to arc 112. Further, one or both of surfaces surface 120 and 126 may, as described above, be concave along one axis or two axes.

Although the concavity of the modules of modular IMD 100 is described with reference to control module 30, it is understood that modules 32 and 34 and any additional or alternative modules may include a housing with a surface that is concave along at least on axis as described herein. For example, in embodiments where power source module 32 includes a battery with a thin wound-coil construction within housing 38 the wound coil is bendable in one direction such that both it and housing 38 may be made concave along one axis. In embodiments where power source module 32 includes a battery with a foil pack construction within housing 38, the foil pack is bendable in two directions such that both it and housing 38 may be made concave along two axes. Further, both housing 40 and a recharge coil 42 formed of windings of copper therein may be made concave along one or two axes.

Figure 10A:
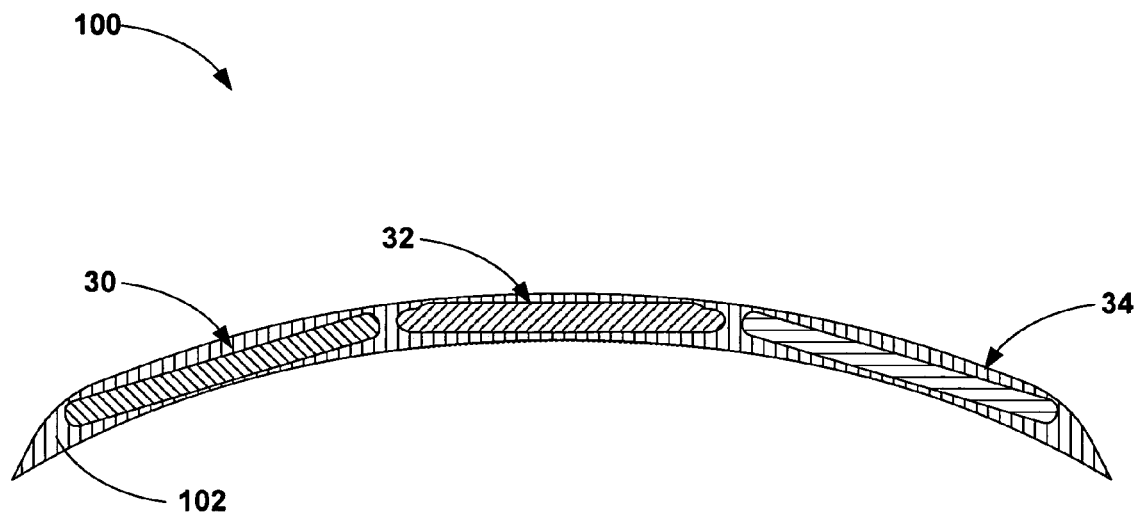
FIGS. 10A and 10B are cross-sectional diagrams of the modular implantable medical device of FIG. 7B illustrating two example configurations of the modular implantable medical device of FIG. 7B.
Figure 10B:
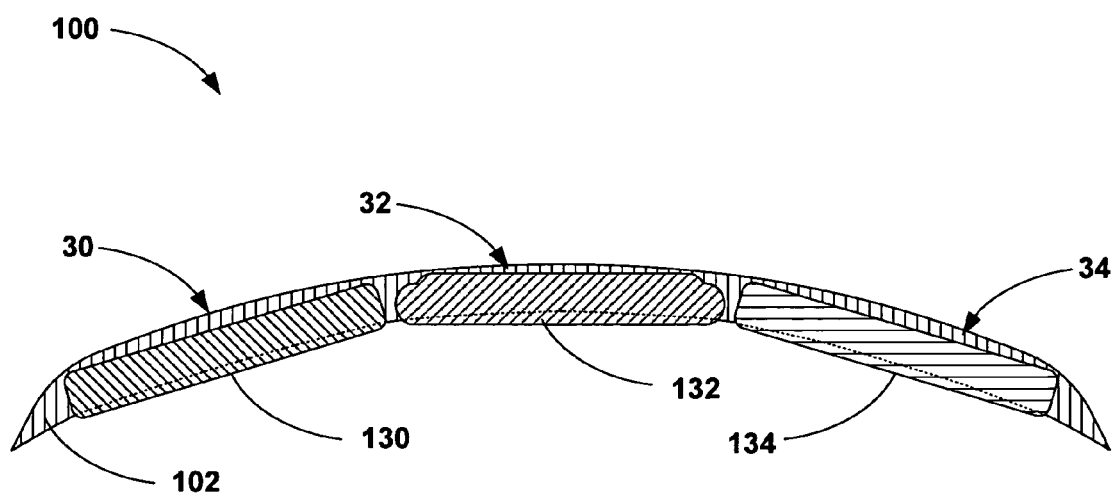

FIGS. 10A and 10B are cross sectional diagrams illustrating two example configurations of overmold 102 of modular IMD 100, the cross-section taken along axis 94 (FIG 7B). FIG. 10A illustrates an embodiment of IMD 100 in which overmold 102 fully encapsulates modules 30, 32 and 34, while FIG 10B illustrates an embodiment of IMD 100 in which overmold 102 partially encapsulates modules 30, 32 and 34. In embodiments where overmold 102 partially encapsulates modules 30, 32 and 34, overmold 102 leaves portions 130, 132 and 134 of modules 30, 32 and 34 exposed, respectively. Portions 130, 132 and 134 may, as illustrated in FIG. 10B, be lower portions of modules 30, 32 and 34, e.g., portions of the modules that are proximate to cranium 12 when modular IMD 100 is implanted thereon. Embodiments in which overmold 102 fully encapsulates modules 30, 32 and 34 may be preferred as providing greater patient comfort and protection of the modules. However, in some embodiments in which portions 130, 132 and 134 are exposed, troughs may be drilled into the surface of cranium 12 that are sized to receive the portions. By recessing portions 130, 132 and 134 into such troughs, the height of modular IMD 100 above cranium 12 may be reduced. As illustrated in FIGS. 10A and 10B, the housings of modules 30, 32 and 34 may be horizontally distributed at respective locations of overmold 102, and overmold 102 may separately encapsulate, either partially or completely, each of the housings.

Various embodiments of the invention have been described. However, one skilled in the art will appreciate that the invention is not limited to the described embodiments, and that modification may be made to the described embodiments without departing from the scope of the claims. For example, although described herein in the context of a modular IMD including flexibly interconnected modules and an overmold, the invention is not so limited. In some embodiments, the interconnections between modules of an IMD are not flexible. Moreover, in some embodiments, an IMD that is not modular comprises a single housing that includes a surface that is concave as described herein. These and other embodiments are within the scope of the following claims.

The invention claimed is:

1. An implantable medical device comprising:
a plurality of interconnected modules, wherein at least one of the interconnected modules comprises a metallic housing, and wherein the plurality of interconnected modules are horizontally distributed such that a space exists between each of the plurality of interconnected modules;
a flexible overmold that at least partially encapsulates each of the interconnected modules such that the flexible overmold separately encapsulates each of the modules and exists with and at least partially fills the space;

a therapy delivery element to deliver a therapy to a brain of a patient; and control electronics to control the delivery of the therapy by the therapy delivery element, wherein the therapy delivery element and control electronics are located within one of the interconnected modules, wherein the flexible overmold is formed such that a surface of the flexible overmold is concave along two perpendicular axes prior to manipulation of the implantable medical device and is adapted to be implanted proximate to a cranium of the patient, and wherein the flexible overmold does not encapsulate at least a portion of the metallic housing.

2. The implantable medical device of claim 1, wherein the overmold comprises silicone.

3. The implantable medical device of claim 1, wherein the overmold comprises at least two materials.

4. The implantable medical device claim 1, wherein the surface of the flexible overmold is concave such that the surface is adapted to conform substantially to the cranium.

5. The implantable medical device of claim 1, wherein he surface of the flexible overmold is concave such that the flexible overmold conforms substantially to an arc, and a radius of the arc is within a range from 4.5 to 9.5 centimeters.

6. The implantable medical device of claim 5, wherein the radius of the arc is approximately equal to 7 centimeters.

7. The implantable medical device of claim 5, wherein the surface comprises a first surface of the flexible overmold, and a second surface of the flexible overmold that is adapted to be implanted distal from the cranium substantially conforms to the arc prior to manipulation of the implantable medical device.

8. The implantable medical device of claim 1, wherein the interconnected modules are positioned within the flexible overmold in one of a triangular configuration and a linear configuration.

9. The implantable medical device of claim 1, wherein at least two of the plurality of interconnected modules each comprise a metallic housing, and wherein the flexible overmold does not encapsulate a portion of each of the at least two metallic housings.

10. The implantable medical device of claim 1, wherein a surface of the metallic housing is adapted to be implanted proximate to the cranium and is concave along at least one axis prior to manipulation of the implantable medical device.

11. The implantable medical device of claim 10, wherein the at least one of the interconnected modules that comprises the metallic housing comprises a control module that includes control electronics, and the surface of the metallic housing of the control module is concave along two perpendicular axes.

12. The implantable medical device of claim 10, wherein the at least one of the interconnected modules that comprises the metallic housing comprises a power source module that includes a battery with a wound coil construction, and the surface of the metallic housing of the power source module and the wound coil battery are each concave along at least one axis prior to manipulation of the implantable medical device.

13. The implantable medical device of claim 10, wherein the at least one of the interconnected modules that comprises the metallic housing comprises a power source module that includes a battery with a foil pack construction, and the surface of the metallic housing of the power source module and the foil pack battery are each concave along at least one axis prior to manipulation of the implantable medical device.

14. The implantable medical device of claim 10, wherein at least one of the interconnected modules comprises a recharge module that includes a recharge coil for inductively receiving energy, and a surface of a housing of the recharge module and the coil are each concave along two perpendicular axes prior to manipulation of the implantable medical device.

15. The implantable medical device of claim 10, wherein the surface of the metallic housing is concave such that the surface is adapted to conform substantially to the cranium.

16. The implantable medical device of claim 10, wherein the surface of the metallic housing is concave such that the surface conforms substantially to an arc, and a radius of the arc is within a range from 4.5 to 9.5 centimeters.

17. The implantable medical device of claim 16, wherein the radius of the arc is approximately equal to 7 centimeters.

18. The implantable medical device of claim 16, wherein the surface of the metallic housing comprises a first surface of the housing, and a second surface of the housing that is adapted to be implanted distal from the cranium conforms substantially to the arc.

19. The implantable medical device of claim 1, wherein the therapy comprises stimulation.

20. The implantable medical device of claim 1, wherein the plurality of interconnected modules comprises at least two modules, each of the modules comprising a metallic housing.

21. The implantable medical device of claim 1, wherein the metallic housing is hermetic and formed of titanium or stainless steel.

22. The medical device of claim 1, further comprising a power source located within the metallic housing.

23. An implantable medical device comprising:

a plurality of interconnected modules, wherein at least one of the interconnected modules comprises a metallic housing, and wherein the plurality of interconnected modules are horizontally distributed such that a space exists between each of the plurality of interconnected modules;

a flexible overmold that at least partially encapsulates each of the interconnected modules such that the flexible overmold separately encapsulates each of the modules and exists with and at least partially fills the space;

a therapy delivery element to deliver a therapy to a brain of a patient; and control electronics to control the delivery of the therapy by the therapy delivery element, wherein the therapy delivery element and control electronics are located within one of the interconnected modules, wherein the flexible overmold is formed such that a surface of the flexible overmold is adapted to be implanted proximate to a cranium of the patient and is concave along two perpendicular axes prior to manipulation of the implantable medical device, and wherein the flexible overmold is configured to allow relative motion between the plurality of interconnected modules.

24. The implantable medical device of claim 23, wherein the therapy comprises stimulation.

* * * * *